United States Patent [19]
Thebrin et al.

[11] Patent Number: 5,938,894
[45] Date of Patent: Aug. 17, 1999

[54] ABSORBENT CELLULOSIC MATERIAL AND PRODUCTION THEREOF

[75] Inventors: Ingemar Thebrin; Svante Wåhlèn, both of Stenungsund; Erik Lindgren, Bohus; Kerstin Malmborg, Hjälteby, all of Sweden

[73] Assignee: Eka Chemicals AB, Bohus, Sweden

[21] Appl. No.: 08/823,445

[22] Filed: Mar. 24, 1997

Related U.S. Application Data

[60] Provisional application No. 60/015,393, Apr. 2, 1996.

[30] Foreign Application Priority Data

Mar. 25, 1996 [SE] Sweden ................................. 9601135

[51] Int. Cl.$^6$ ......................... D21H 21/22; D21H 17/68
[52] U.S. Cl. ..................... 162/181.6; 162/181.1; 162/181.7
[58] Field of Search ................. 162/157.2, 158, 162/181.1, 182, 181.6, 181.7

[56] References Cited

U.S. PATENT DOCUMENTS

| | | | |
|---|---|---|---|
| 4,289,513 | 9/1981 | Brownhill et al. | 55/387 |
| 4,826,497 | 5/1989 | Marcus et al. | 604/359 |
| 4,900,377 | 2/1990 | Redford et al. | 156/62.2 |
| 5,611,890 | 3/1997 | Vinson et al. | 162/111 |

FOREIGN PATENT DOCUMENTS

| | | | |
|---|---|---|---|
| 0 540 076 | 5/1993 | European Pat. Off. | D21H 17/68 |
| WO 91/11977 | 8/1991 | WIPO | A61F 13/15 |

OTHER PUBLICATIONS

PCT International Search Report, Jul. 8, 1997.

*Primary Examiner*—Peter Chin
*Assistant Examiner*—Steven B. Leavitt
*Attorney, Agent, or Firm*—Ralph J. Mancini

[57] ABSTRACT

A method in which a sheet of cellulosic fibres is shredded into fluff wherein, prior to shredding, the fibres are treated in the presence of water with a hydrophobic substance having a specific surface area of at least about 50 $m^2/g$, to yield improved sorptive capacity; fluff obtainable by the method; absorbent articles comprising such fluff; use of a substance of said kind for improving the sorptive capacity of absorbent material comprising the fibers; a process for production of absorbent material obtained by shredding a sheet of such fibers in which the fibers, prior to shredding, have been treated in the presence of water with a substance of said kind to yield improved sorptive capacity; and absorbent material obtainable from the process.

13 Claims, No Drawings

ABSORBENT CELLULOSIC MATERIAL AND PRODUCTION THEREOF

This present application claims priority of Swedish patent application no. 9601135-8 filed on Mar. 25, 1996 and benefit of U.S. provisional application no. 60/015,393 filed Apr. 2, 1996 under 35 U.S.C. §119.

FIELD OF INVENTION

The present invention relates to a method for production of fluff having improved sorptive capacity, and to fluff obtainable by such a method. The invention also relates to the use of hydrophobic substances having a specific surface area of more than 50 $m^2/g$ for treatment of cellulosic fibres to improve the sorptive capacity of absorbent material comprising the fibres. Furthermore, the invention relates to a process for production of an absorbent material comprising cellulosic fibres obtained by shredding or fluffing a pulp sheet, which structure has improved sorptive capacity.

BACKGROUND OF THE INVENTION

In the present context the concept of "sorptive capacity" aims at the rate by which the absorbent material takes up liquids such as water or aqueous solutions, including body fluids such as urine, blood and menstrual fluids, or to the liquid-retaining capacity of the absorbent material, or to both of these characteristics. The sorptive mechanism may be adsorption or absorption, or a combination thereof.

As stated in Pulp and Paper Manufacture, Vol. 2, page 280–281, Joint Textbook Committee of the Paper Industry, 1987, hereby incorporated by reference, the term fluff applies to fibres which have been separated by mechanical means from dry pulps for application in dry-formed non-woven webs or pads in the household or sanitary fields. As is evident from this reference both the rate of liquid uptake and liquid-holding capacity of fluff are important when used in these fields. This is particularly valid with regard to absorbent articles such as catamenial devices (e.g. sanitary napkins, pantiliners, tampons etc.), diapers, bandages, adult incontinence garments, and the like; good liquid uptake and liquid-holding capacity are obvious prerequisites for the function of such articles. However, when used, an article of this kind is constantly subjected to pressure imposed by the weight and the movements of the bearer, and thus it is important that the liquid-holding capacity is high enough to retain the absorbed liquid also under pressure. Furthermore, in order to give good comfort to the bearer, the article should provide a feeling of dryness, meaning that any rewetting from the article to the skin of the bearer should by avoided, raising the requirements with regard to liquid-holding capacity even higher. Conventionally, certain polymeric materials forming hydrogels in contact with water, known as "superabsorbents", have been utilised to enhance the sorptive capacity of such articles; however, although this capacity of the article is enhanced, as the liquid is bound to superabsorbent particles, the sorptive capacity of the cellulosic fibres making up the fluff itself is not in fact enhanced by the use of such superabsorbents.

The problem to be solved by the present invention is thus to provide a method for production of fluff having improved sorptive capacity.

That problem is solved by the method defined by the appended claims.

The reason why hydrophobic substances of the stated kind impose improved sorption characteristics has so far not been clearly established.

SUMMARY OF INVENTION

The present invention generally relates to a method for production of absorbent material having improved sorptive capacity, which material comprises cellulosic fibres, wherein said method comprises treating said fibres, in the presence of water, with a hydrophobic substance having a specific surface area of at least 50 $m^2/g$, wherein the treatment comprises contacting said substance and said fibres together when the fibres have a dry content of at least 20%.

DETAILED DESCRIPTION OF THE INVENTION

In the present method a sheet of cellulosic fibres is shredded into fluff; in this context a "sheet" means a sheet or a web. The formation of the sheet, below referred to as "the pulp sheet", may follow either one of the paths for such formation known in the art, e.g. the wet method analogous to conventional paper making, or the flash drying method, both methods described in Pulp and Paper Manufacture, Vol. I, page 753–757, Joint Executive Committee of Vocational Education Committees of the Paper Industry, 1969, hereby incorporated by reference.

To "treat" the fibres with a hydrophobic substance means that particles of the substance are brought into the proximity of, or in contact with the fibres; preferably, the particles are kept in the proximity of, or in contact with, the fibres for at least about 1 minute, suitably at least about 30 seconds, and particularly at least about 5 seconds. The treatment may be carried out at any point within the process starting with the separation of the fibres from each other and ending with dry shredding of the pulp sheet. Preferably, however, the treatment is carried out when the dry matter content of the fibres is at least about 25%, suitably at least about 35%, and most preferably at least about 50%.

The specific surface area of the hydrophobic substance particles, determined according to standard method DIN 66131 modified as described below, is at least about 50 $m^2/g$, preferably at least about 100 $m^2/g$, and most preferably at least about 1000 $m^2/g$.

The hydrophobic substance may be any substance that is substantially insoluble in water, preferably having a solubility not higher than about 1 g/100 g of water, suitably not higher than about 0.1 g/100 g of water, as long as it has a specific surface area as indicated above. Exemplary of useful hydrophobic substances are activated carbon, hydrophobic zeolites, and polytetrafluoroethylene (i.e. Teflon). The substances are preferably porous. In a particularly preferred embodiment the hydrophobic substance is activated carbon or a zeolite having a hydrophobicity of below about 0.99 percent, preferably below about 0.90 percent, and suitably below about 0.70 percent by weight residual butanol as determined by the Residual Butanol Test described below. Especially preferred zeolites are those having a molar relation $SiO_2/Al_2O_3$ of at least 5.

Although the hydrophobic substance may be brought to the fibres in a dry as well as a wet state, it is preferred that the substance is comprised in an aqueous mixture, usually as a dispersion or a slurry. The mixture is suitably applied on the formed pulp sheet, conveniently by spraying. The amount of substance added is suitably about 0.1–10 kg/metric ton dry pulp, preferably about 0.5–5 kg/ton. Optionally the treatment may be carried out when the fibres are suspended in an aqueous solution, e.g. in the stock of the pulp production process prior to forming the sheet; the amount of substance in the stock is suitably about 0.1–10 kg/ton dry pulp, preferably about 0.5–5 kg/ton.

The treatment may be carried out in the presence of a retention agent to ensure that a sufficient amount of the substance particles are kept in contact with, or in the proximity of the fibres long enough to give the desired effect. Exemplary of preferred retention agents are polysaccharides, such as starch, cellulose derivatives, xanthan gum and guar gum, and synthetically produced homopolymers, such as polyacryl amide (PAM), polyamide amine (PAA), polydiallyl dimethyl ammonium chloride (polyDADMAC), polyethylene imine (PEI) and polyethylene oxide (PEO), or copolymers thereof.

Although the substance may remain in the fluff after shredding, this is not considered to be essential to the invention. In fact, even if less than about 65%, say less than 30%, or even as little as about 1% of the substance used in the treatment is present in the fluff after shredding, the sorption effect is quite noticeably enhanced when compared to fluff produced from untreated pulp. In some instances it may however be advantageous to let a substantial amount of substance remain in the fluff, for instance when the substance is a hydrophobic zeolite providing such odour eliminating characteristics to absorbent articles, e.g. diapers and catamenial devices, as disclosed in U.S. Pat. No. 4,826,497 and WO 91/11977; it should, however, be noted that in those documents the zeolite is either used in positions separated from the fluff, or mixed with the fluff after shredding.

The present invention also relates to fluff obtainable by the present method. As is evident from the below examples such fluff shows surprisingly good sorption characteristics when compared to fluff mixed with zeolite or activated carbon according to prior art, i.e. after shredding. The cause of this enhanced effect is unknown, but is obviously due to some characteristic of the fluff imposed by the specific method of application.

The invention also relates to the use of a hydrophobic substance of the present kind for treatment of cellulosic fibres to improve the sorptive capacity of absorbent materials comprising the fibres, such as for instance fluff or hygienic paper, e.g. soft tissue. It furthermore relates to a process for the production of absorbent material, including for instance dry-formed nonwoven or tissue, that comprises cellulosic fibres treated as stated above with a hydrophobic substance prior to fluffing; it also relates to absorbent articles, such as sanitary napkins, pantiliners, tampons, diaper bandages, adult incontinence garments, and the like, in which fluff obtainable by the present method is used.

The fibres making up the pulp sheet are usually obtained by disintegrating wood, conventionally in the form of chips, into fibres or bundles of fibres; in the present context the concept of "bundles of fibres" is regarded to be equivalent to the concept of "fibres". The separated fibres may be obtained by means of any pulp-making method known to a skilled person, e.g. by a method for production of mechanical pulp (MP), stone groundwood pulp (SGW), pressure groundwood pulp (PGW), refiner mechanical pulp (RMP), thermo-mechanical pulp (TMP), chemi-mechanical pulp (CMP), or chemi-thermomechanical pulp (CTMP), although the preferred pulps are chemical pulps such as, for instance, sulphate and sulphite pulps. However, the cellulosic fibres may also advantageously be cotton fibres. Another plausible source of fibres is recycled fibres from wastepaper.

The present invention is illustrated in more detail below by means of examples. Unless otherwise stated the parts and percentages below are given by weight. In the examples the substances according to table I were used; substances A to N are zeolites and substance O is an activated carbon.

TABLE I

| Substance | hydrophobicity, % | molar relation $SiO_2/Al_2O_3$ | type |
|---|---|---|---|
| A | 0.03 | 900 | ZSM-5 |
| B | 0.14 | 35 | ZSM-5 |
| C | 0.15 | 35 | ZSM-5 |
| D | 0.24 | 29 | Y |
| E | 0.27 | 25 | Y |
| F | 0.28 | 29 | Y |
| G | 0.30 | 5.1 | Y |
| H | 0.46 | 12 | Y |
| I | 0.81 | 5.2 | Y |
| J | 0.81 | 5.2 | Y |
| K | 0.83 | 5.5 | Y |
| L | 0.99 | 2.6 | X |
| M | 0.99 | 2 | A |
| N | 0.99 | 2 | A |
| O |  |  | activated carbon |

The hydrophobicities of the zeolites indicated in Table I are determined by a so-called Residual Butanol Test, described in GB 2,014,970. In this test, the zeolite is activated by heating in air for 16 h at 300° C. Then, 10 parts by weight of the thus-activated zeolite are mixed with a solution consisting of 1 part by weight of I-butanol and 100 parts by weight of water. The resulting slurry is slowly agitated for 16 h at 25° C. Finally, the residual content of I-butanol in the solution is determined and indicated in per cent by weight. Thus, a low value indicates a high degree of hydrophobicity.

Activated carbon is the collective name for a group of porous carbons manufactured either by treatment of carbon with gases, or by carbonisation of carbonaceous materials with simultaneous activation by chemical treatment; a more detailed description of activated carbons is given in "Ullmann's encyclopedia of industrial chemistry" (Vol. A 5, page 124 and onwards), 1986, hereby incorporated by reference.

The specific surface areas were determined by a method based on DIN 66131 (July 1993), the so-called BET method, in which the areas were determined by using one point of the adsorption isotherm at a relative pressure $p/p_0$ of 0.03, p being the pressure of the gas adsorbed in that method and $p_0$ being the saturation vapour pressure for the same gas. For activated carbon the specific surface area was about 1000 m2/g, for zeolite of type ZSM-5 and type A it was about 500 m2/g, whereas zeolite X and Y each showed a specific surface area of about 800 m2/g.

In the Examples below, the fluff obtained was tested with respect to rewetting, and in some Examples also with respect to the uptake rate. The test method for determination of the uptake rate was SCAN-C 33:80, in which fluff samples of 3 g having a diameter of 50 mm are positioned vertically and loaded with a weight of 500 g on top. The sample is allowed to absorb water from below, and the time taken until water penetrates through the upper surface of the sample is determined automatically by means of an electronic detector. The shorter time required to penetrate the upper surface, the higher is the uptake rate of the fluff. In the test method for determination of rewetting or liquid holding capacity a fluff sample of 3 g having a diameter of 50 mm is positioned vertically and loaded with a weight of 1 kg on top for 30 s, and is then unloaded. 10 ml of water is applied to the sample under a time period of 10 s and the liquid is allowed to drain the sample for 30 s, whereafter the sample is loaded with a weight of 1 kg for 4 minutes. 15 sheets, 8×8 cm, of filter paper are placed on top of the sample, and the combined sample and sheets are loaded with a weight of 5 kg for one additional minute, after which the 15 sheets are weighed. The increase of weight of the sheets is due to rewetting. Thus, a low weight increment indicates low rewetting.

EXAMPLES 1–14

10 g sulphate pulp was slushed for 10 minutes in 500 ml water in a laboratory pulper. The thus obtained stock was dewatered through the screen cloth of a wire mould, producing pulp sheets having diameters of 210 mm. 15 g of aqueous solutions containing 0.2% hydrophobic substance were sprayed onto the sheets in all examples except for Example 1, which is a comparison example. The amount of hydrophobic substance added to each sheet corresponded to 3 kg substance/ton of dry pulp. The sheets were dried at 60° C. for 120 minutes and then dry shredded into fluff in a hammer mill. The fluff was formed into three samples, each of 3 g. The fluff samples thus obtained were tested, at ambient conditions of about 23° C. and 50% RH, with regard to rewetting as is set forth in Table II below.

TABLE II

Sulphate Pulp, 3 kg hydrophobic substance/metric ton pulp

| | substance added by spraying | |
|---|---|---|
| substance | Ex | rewetting, g |
| Ref | 1 | 5.0 |
| A | 2 | 4.5 |
| B | 3 | 4.2 |
| C | 4 | 4.4 |
| D | 5 | 4.0 |
| F | 6 | 3.2 |
| G | 7 | 3.8 |
| H | 8 | 4.1 |
| I | 9 | 4.2 |
| J | 10 | 4.7 |
| L | 11 | 4.5 |
| M | 12 | 4.1 |
| N | 13 | 4.4 |
| O | 14 | 4.4 |

The fluff produced according to the present method evidently has a better liquid retaining capacity than untreated fluff.

EXAMPLES 15–21

The procedure used in Examples 1–14 was repeated, except that the hydrophobic substance was added during slushing instead of being sprayed. Here Example 15 is the comparison example, i.e. without any hydrophobic substance added. The fluff samples obtained were tested with regard to rewetting as is set forth in Table III below.

TABLE III

Sulphate Pulp, 3 kg hydrophobic substance/ton pulp

| | substance added by spraying | |
|---|---|---|
| substance | Ex | rewetting, g |
| Ref | 15 | 5.0 |
| B | 16 | 4.8 |
| C | 17 | 4.5 |
| D | 18 | 4.5 |
| F | 19 | 4.6 |
| G | 20 | 4.2 |
| I | 21 | 4.7 |

The fluff produced according to the present method evidently has a better liquid retaining capacity than untreated fluff.

EXAMPLES 22–26

The procedure outlined with regard to Examples 1–14 was repeated, although applied on sulphite pulp. Example 22 is a comparison example with no hydrophobic substance added. The results are set forth in Table IV below.

TABLE IV

Sulphate Pulp, 3 kg hydrophobic substance/ton pulp

| | substance added by spraying | |
|---|---|---|
| substance | Ex | rewetting, g |
| Ref | 22 | 5.15 |
| C | 23 | 4.37 |
| F | 24 | 4.22 |
| L | 25 | 4.84 |
| N | 26 | 4.55 |

The fluff produced according to the present method evidently has a better liquid retaining capacity than untreated fluff.

EXAMPLES 27–29

The procedure outlined with regard to Examples 1–14 was repeated, although applied on chemi-thermomechanical pulp (CTMP); uptake rates were also determined. Example 27 is a comparison example with no hydrophobic substance added. The results are set forth in Table V below.

TABLE V

CTMP, 3 kg hydrophobic substance/ton pulp

| | substance added by spraying | | |
|---|---|---|---|
| substance | Ex | uptake rate, s | rewetting, g |
| Ref | 27 | 12 | 5.00 |
| C | 28 | 11 | 4.32 |
| F | 29 | 8.2 | 4.41 |

The fluff produced according to the present method evidently has a faster uptake rate and a better liquid retaining capacity than untreated fluff.

EXAMPLES 30–32

The procedure outlined with regard to Examples 1–14 was repeated, although applied on cotton; uptake rates were also determined. Example 30 is a comparison example with no hydrophobic substance added. The results are set forth in Table VI below.

TABLE VI

Cotton, 3 kg hydrophobic substance/ton pulp

| | substance added by spraying | | |
|---|---|---|---|
| substance | Ex | uptake rate, s | rewetting, g |
| Ref | 30 | 5.1 | 6.54 |
| C | 31 | 4.6 | 6.24 |
| F | 32 | 4.4 | 6.00 |

The fluff produced according to the present method evidently has a faster uptake rate and a better liquid retaining capacity than untreated fluff.

EXAMPLES 33–38

The procedure outlined with regard to Examples 1–14 was repeated, although in the test method for determination of rewetting an aqueous solution the properties relevant for the test of which were similar to those of blood was used. This solution contained 10 g/l of NaCl, 80 g/l of glycerol, 4 g/l of NaHCO$_3$; the viscosity of the solution was adjusted to about 12 cP by adding carboxymethyl cellulose (CMC), and the surface tension was adjusted to about 50 mN/m by adding a nonionic surfactant. Example 33 is a comparison example with no hydrophobic substance added. The results are set forth in Table VII below.

TABLE VII

Sulphate Pulp, 3 kg hydrophobic substance/ton pulp

| | substance added by spraying | |
|---|---|---|
| substance | Ex | rewetting, g |
| Ref | 33 | 4.50 |
| E | 34 | 3.81 |
| F | 35 | 3.60 |
| H | 36 | 3.96 |
| K | 38 | 4.26 |

Thus, also with regard to blood the fluff produced according to the present method has a better liquid retaining capacity than untreated fluff.

EXAMPLE 39 substance F was added to sulphate pulp, directly to the stock or by spraying a pulp sheet. The treated pulp was then shredded into fluff, and the remaining content of substance F in the fluff was determined. Furthermore a comparative test, according to prior art, in which dry substance F was applied to dry-shredded sulphate pulp (i.e. fluff) was carried out. These three fluff samples were tested with regard to rewetting. The results are set forth in Table VIII below.

TABLE VIII

| Application method | Added amount of substance, F, kg/t | Remaining amount of substance F in fluff, kg/t | Rewetting, g |
|---|---|---|---|
| Dry hydrophobic substance on dry fluff (prior art) | 0.6 | 0.6 | 4.56 |
| Addition to stock | 3 | 0.6 | 4.44 |
| Addition by spraying | 1 | 0.6 | 4.35 |

Although the three obtained fluff products contained the same amount of substance F, their properties were thus clearly different, as evidenced by the fact that the fluff produced according to the present method had significantly better rewetting characteristics.

We claim:

1. A method for production of fluff having improved take-up rate and/or liquid-retaining capacity for aqueous solutions from shredded cellulose fibers, wherein prior to shredding the cellulose fibers, the fibers are treated in the presence of water with a hydrophobic zeolite having a specific surface area of at least about 50 m$^2$/g.

2. The method of claim 1 wherein prior to the treatment the fibres have an dry content of at least about 20%.

3. The method of claim 1 wherein the hydrophobic zeolite has a hydrophobicity of below about 0.99 percent by weight residual butanol as determined by the Residual Butanol Test.

4. The method of claim 1 wherein the fibres are sprayed or showered with a mixture comprising the substance and water.

5. The method of claim 1 wherein the fibres are suspended in an aqueous solution during the treatment, prior to forming the sheet.

6. Fluff prepared in accordance with the method of claim 1.

7. An absorbent article comprising fluff according to claim 6.

8. A method for improving the take-up rate and/or liquid-retaining capacity for aqueous solutions of an absorbant material comprising cellulose fibers obtained by shredding a sheet of such fibers which comprises treating the fibers of said absorbant material prior to shredding with a hydrophobic zeolite having a specific surface area of more than 50 m$^2$/g.

9. The method of claim 8 wherein the hydrophobic zeolite has a hydrophobicity of below about 0.99 percent by weight residual butanol as determined by the Residual Butanol Test.

10. A process for the production of absorbent material comprising cellulosic fibers obtained by shredding a sheet of such fibers, which structure has improved take-up rate and/or liquid-retaining capacity for aqueous solutions, wherein prior to shredding said sheet, the cellulose fibers are treated in the presence of water with a hydrophobic zeolite having a specific surface area of at least 50 m$^2$/g.

11. Absorbant material prepared in accordance with the process of claim 10.

12. Absorbant material according to claim 11 wherein the material is dry-formed nonwoven or tissue.

13. Absorbant material according to claim 11 wherein the material is fluff.

* * * * *